United States Patent
Duffy et al.

(10) Patent No.: US 11,827,584 B2
(45) Date of Patent: Nov. 28, 2023

(54) PROCESS FOR PREPARING CYANOACETATES

(71) Applicant: Henkel AG & Co. KGaA, Duesseldorf (DE)

(72) Inventors: Cormac Duffy, County Louth (IE); Justine O'Sullivan, County Kildare (IE); Ciara Goff, County Wexford (IE); Umar Farid, Dublin (IE); Jessica Ramos, County Kildare (IE); Michael Thai Trung King, Dublin (IE); Isidro Cobo Cardenete, Dublin (IE); Marisa Phelan, Dublin (IE); Barry Burns, Dublin (IE)

(73) Assignee: Henkel AG & Co. KGaA, Duesseldorf (DE)

( * ) Notice: Subject to any disclaimer, the term of this patent is extended or adjusted under 35 U.S.C. 154(b) by 123 days.

(21) Appl. No.: 17/451,279

(22) Filed: Oct. 18, 2021

(65) Prior Publication Data

US 2022/0033349 A1   Feb. 3, 2022

Related U.S. Application Data

(63) Continuation of application No. PCT/EP2020/060886, filed on Apr. 17, 2020.

(30) Foreign Application Priority Data

Apr. 18, 2019  (GB) ..................................... 1905579

(51) Int. Cl.
| | |
|---|---|
| *C07C 253/00* | (2006.01) |
| *C07C 253/34* | (2006.01) |
| *C07C 227/18* | (2006.01) |
| *C07C 227/40* | (2006.01) |

(52) U.S. Cl.
CPC .......... *C07C 253/00* (2013.01); *C07C 227/18* (2013.01); *C07C 227/40* (2013.01); *C07C 253/34* (2013.01)

(58) Field of Classification Search
None
See application file for complete search history.

(56) References Cited

U.S. PATENT DOCUMENTS

| | | | |
|---|---|---|---|
| 2,721,858 A | 10/1955 | Joyner et al. | |
| 2,756,251 A | 7/1956 | Joyner et al. | |
| 2,763,677 A | 9/1956 | Jeremias | |
| 4,202,920 A | 5/1980 | Margotte et al. | |
| 4,364,876 A | 12/1982 | Kimura et al. | |
| 4,512,357 A | 4/1985 | Earl | |
| 4,888,440 A | 12/1989 | Wilschowitz | |
| 5,624,699 A | 4/1997 | Lang | |
| 6,245,933 B1 | 6/2001 | Malofsky et al. | |

FOREIGN PATENT DOCUMENTS

| | | |
|---|---|---|
| EP | 0459617 | 12/1991 |
| GB | 2558256 | 7/2018 |
| JP | 2003238510 | 8/2003 |
| WO | 0116092 | 3/2001 |

OTHER PUBLICATIONS

PCT International Search Report issued in connection with International Application No. PCT/EP2020/060886 dated Jul. 13, 2020.
Tetrahedron: Asymmetry, vol. 14, No. 15, 2003, pp. 2133-2142 Wu & Li, "Enantioselective biotransformation of a, a-disubstituted dinitriles to the corresponding 2-cyanoacetamides using *Rhodococcus* sp. CGMCC 0497"—See whole document, especially compound 2a.
Green Chemistry, vol. 13, No. 4, 2011, pp. 807-809 Le Notre et al., "Biobased synthesis of acrylonitrile from glutamic acid"—See whole document, especially Scheme 4.
Vijayalakshmi et al., J. Ad. Sci. Technol., 4, 9, 733 (1990).
Guseva et al., Russia Chem. Bull., 42, 3, 478 (1993).
Guseva et al., Russia Chem. Bull., 43, 4, 595 (1994).
Golobolov and Gruber, Russia Chem. Rev., 66, 11, 953 (1997).
Senchenya et al., Russia Chem. Bull, 42, 5, 909 (1993).
Renner et al., "Cure of Epoxy Resins with Esters of Cyanoacrylic Acid", J. Polym. Sci., Poly. Chem. Ed., 23, 2341 (1985).
K. Sato et al., Chem. Comm., 51, 9946-48 (2015).
G. Hiegel et al., Synth. Commun., 34, 3449-53 (2004).
L. De Luca, et al., "An Insight of the reactions of amines with trichloroisocyanuric acid", No. 12, pp. 2180-2184 (2004).
N. Ouwerkerk et al., :Synthesis of [1', 2', 5', 2-13C4]-2'-deoxy-D-adenosine by a chemoenzymatic strategy to enable labelling of any of the 215 carbon-13 and nitrogen 15 isotopmers, European Journal of Organic Chemistry, No. 14, pp. 2356-2362 (2002).

*Primary Examiner* — Samantha L Shterengarts
(74) *Attorney, Agent, or Firm* — Steven C. Bauman

(57) ABSTRACT

This invention relates to a process for producing cyanoacetates using aspartic acid as a precursor.

24 Claims, No Drawings

PROCESS FOR PREPARING CYANOACETATES

BACKGROUND

Field

This invention relates to a process for producing cyanoacetates using aspartic acid as a precursor.

Brief Description of Related Technology

Cyanoacrylate adhesives are known for their fast adhesion and ability to bond a wide variety of substrates. They are marketed as "super glue" type adhesives. They are useful as an all-purpose adhesive since they are a single component adhesive, very economical as only a small amount will do, and generally do not require any equipment to effectuate curing.

Traditionally, cyanoacrylate monomers have been produced by way of a Knoevenagel condensation reaction between a formaldehyde precursor, such as paraformaldehyde, and an alkyl cyanoacetate with a basic catalyst. During the reaction, cyanoacrylate monomer forms and polymerises in situ to a prepolymer. The prepolymer is subsequently thermally cracked or depolymerised, yielding cyanoacrylate monomer. This approach has remained essentially the same over time, though various improvements and variants have been introduced. See e.g. U.S. Pat. Nos. 6,245,933, 5,624,699, 4,364,876, 2,721,858, 2,763,677 and 2,756,251. Thus, it is seen one use of cyanoacetates is in the formation of cyanoacrylates.

Vijayalakshmi et al., *J. Ad. Sci. Technol.*, 4, 9, 733 (1990) describes some approaches to the synthesis of cyanoacetates and corresponding cyanoacrylates, including preparation from chloroacetic acid and its esters by subsequent reaction with sodium cyanide.

Guseva et al., *Russia Chem. Bull.*, 42, 3, 478 (1993) describes functionalized cyanoacetates, many of which were used in the subsequent synthesis of corresponding cyanoacrylates. [See also Guseva et al., *Russia Chem. Bull.*, 43, 4, 595 (1994), and Golobolov and Gruber, *Russia Chem. Rev.*, 66, 11, 953 (1997).] Cyanoacetates with siliconised functionalities have been described. See e.g. Senchenya et al., *Russia Chem. Bull.*, 42, 5, 909 (1993) and European Patent Document No. EP 0 459 617.

The preparation of mono-, di-, tri- and tetra-functional cyanoacetates, albeit as curatives for epoxy resins for adhesive applications, has been described. Renner et al., "Cure of Epoxy Resins with Esters of Cyanoacrylic Acid", *J. Polym. Sci., Polym. Chem. Ed.*, 23, 2341 (1985) and U.S. Pat. Nos. 4,202,920 and 4,512,357.

None of these cyanoacetate syntheses use an amino acid as a starting material.

It would be desirable to find alternative synthetic approaches to making cyanoacetates, particularly if such approaches used readily available and inexpensive starting materials like amino acids. It would be even more desirable if such approaches generated the subject cyanoacetate in high yield, was readily isolated, and used at least starting materials that are naturally occurring and recognized as being safe.

SUMMARY

At a high level, the inventive process provides for the preparation of a cyanoacetate, steps of which comprise:

(a) contacting aspartic acid with an alcohol, in the presence of an acetyl halide, under appropriate conditions and for a time sufficient to yield a beta-ester of the aspartic acid;

(b) optionally, separating therefrom the so formed beta-ester of the aspartic acid;

(c) contacting the beta-ester of the aspartic acid with a halogenating agent under appropriate conditions and for a time sufficient to yield a cyanoacetate; and (d) optionally, separating therefrom the so formed cyanoacetate. Either or both of the separation steps should yield product substantially free from the aspartic acid and the acetyl halide, and/or in the case of step (d) halogenating agent, and by-products from steps (a) and/or (c).

DETAILED DESCRIPTION

As noted above, the present invention provides a process for the preparation of a cyanoacetate, steps of which comprise:

(a) contacting aspartic acid with an alcohol, in the presence of an acetyl halide, under appropriate conditions and for a time sufficient to yield a beta-ester of the aspartic acid;

(b) optionally, separating therefrom the so formed beta-ester of the aspartic acid;

(c) contacting the beta-ester of the aspartic acid with a halogenating agent under appropriate conditions and for a time sufficient to yield a cyanoacetate; and (d) optionally, separating therefrom the so formed cyanoacetate. Either or both of the separation steps should yield product substantially free from the aspartic acid, the acetyl halide, and/or in the case of step (d) halogenating agent, and by-products.

The cyanoacetate formed by the inventive process may be a $C_{1-20}$ alkyl cyanoacetate, a $C_{6-20}$ aryl cyanoacetate, a $C_{7-20}$ alkaryl cyanoacetate or a $C_{7-20}$ aralkyl cyanoacetate, any of which may be substituted by one or more hydroxyl groups or $C_{1-20}$ alkyl ether groups.

More specifically, the cyanoacetate may be a $C_{1-20}$ alkyl cyanoacetate, where the $C_{1-20}$ alkyl may be straight chain or branched, contain one or more points of unsaturation and may be substituted and/or interrupted by one or more heteroatoms or heteroatom-containing groups (such as trimethylsilyl alkyl, like methyl, ethyl or propyl), or substituted by halogens or substituted or interrupted by halogen-containing groups. For instance, the cyanoacetate may be methyl, ethyl, propyls (like n-propyl or iso-propyl), propargyl, butyls (like n-butyl or iso-butyl), pentyls (like n-pentyl or iso-amyl), hexyl, octyls (like n-octyl or 2-ethylhexyl), nonyl, oxononyl, decyl, dodecyl, allyl, ethynyl, butenyl, cyclohexyl, tetrahydrofurfuryl, chloroethyl, 2,2,2-trifluoroethyl, hexafluoroisopropyl, alkoxy ether alkyl cyanoacetates (such as methoxymethyl, methoxyethyl, methoxybutyl, ethoxyethyl, propoxyethyl, butoxymethyl, or butoxyethyl) and dimethyl siloxane esters of 2-cyanoacetic acid. This recitation is by no means however exhaustive.

The cyanoacetate may also be a $C_{6-20}$ aryl cyanoacetate such as phenyl cyanoacetate.

Or, the cyanoacetate may be a $C_{7-20}$ aralkyl cyanoacetate such as from phenethyl cyanoacetate, benzyl cyanoacetate, or toluyl cyanoacetate.

In conducting the process, aspartic acid is the starting material or precursor to the cyanoacetate.

The aspartic acid should be used in an amount of about 1 equivalent to the other starting material(s) and reagent(s). The term "equivalent" is intended to capture molar equivalent, whenever it is used herein.

An alcohol is used to perform the esterification of step (a). The alcohol chosen may be an alkyl alcohol, an aryl alcohol, an alkaryl alcohol or an aralkyl alcohol. The identity of the chosen alcohol depends on the desired cyanoacetate sought to be prepared. Accordingly, the alcohol may be selected from methanol, ethanol, propanols (such as isopropanol), proparganols, butanols (such as isobutanol), pentanols (such as isoamyl alcohol), hexanols, octanols, nonanols, oxononanols, decanols, dodecanols, allanol, cyclohexanol, tetrahydrofurfurol, chloroethanol, 2,2,2-trifluoroethanol, hexafluoroisopropanol, alkoxy ether alkanols (such as methoxymethanol, methoxyethanol, methoxybutanol, ethoxyethanol, propoxyethanol, butoxymethanol, or butoxyethanol), dialkyl siloxanols (such as dimethyl siloxanol or diethyl siloxanol), trialkylsilylalkanols (such as trimethylsilylmethanol, trimethylsilylethanol or trimethylsilylpropanol), should the corresponding respective alkyl cyanoacetate ester sought to be produced. Or, if the chosen alcohol is an aromatic alcohol, such as phenol, benzyl alcohol or derivatives thereof, then the corresponding aryl cyanoacetate ester would be the desired product.

The alcohol should be used in an amount of about 5 to about 25 equivalents, such as about 10 to about 20 equivalents, desirably about 12 to about 17 equivalents.

The acetyl halide used in the inventive process may be selected from acetyl bromide or acetyl chloride.

The acetyl halide should be used in an amount of about 1 to about 5 equivalents, such as about 2 to about 4 equivalents, desirably about 2 to about 3 equivalents.

For each equivalent of the beta-ester of the aspartic acid formed in step (a) between about 12 and about 17 equivalents of alcohol and between about 2 to about 3 equivalents of acetyl halide should be used, relative to 1 equivalent of aspartic acid.

The conditions for step (a) should be about room temperature and a time period of about 8 hours to about 24 hours, such as about 12 to about 15 hours.

It is important that in conducting the inventive process, an esterification be performed [such as in step (a)] prior to the oxidative decarboxylation [such as in step (c)]. And not just any esterification, but a selective esterification of the distal or beta carboxylic acid, leaving the alpha carboxylic acid largely unreacted.

Thus, selective esterification conditions are chosen for step (a). That is, the beta-ester of the aspartic acid should be formed preferentially to an alpha-ester of the aspartic acid. Accordingly, appropriate conditions to achieve such selective esterification need to be chosen and are recited above and shown in the Examples.

Thus, the beta-ester of the aspartic acid formed may be a beta-alkyl ester, such as the beta-methyl ester of aspartic acid, the beta-ethyl ester of aspartic acid, a beta-propyl ester of aspartic acid, a beta-butyl ester of aspartic acid, a beta-pentyl ester of aspartic acid, a beta-octyl ester of aspartic acid, a beta-alkoxy ether ester of aspartic acid, or a beta-allyl ester of aspartic acid, for instance.

The beta-ester of the aspartic acid may be a beta-aryl ester, such as beta-phenyl ester of aspartic acid or a beta-phenethyl ester of aspartic acid.

The yield of the beta-ester of aspartic acid should be greater than about 80%, such as greater than about 90%, desirably above about 95%.

Once the beta-ester of aspartic acid has been formed in step (a), that beta-ester may be separated from the reaction mixture or the reaction may be continued without isolating the beta-ester.

Thus, the beta-ester of the aspartic acid once formed, whether or not isolated and/or separated from the reaction mixture of step (a), is contacted with a halogenating agent under appropriate conditions (oftentimes basic conditions) and for a time sufficient to yield a cyanoacetate.

The halogenating agent used in the inventive process may be selected from trihaloisocyanuric acid, N-halosuccinimide, hypochlorites and N-halo-p-toluenesulfonamide salts.

When the halogenating agent is a trihaloisocyanuric acid, the halogenating agent may be selected from tribromoisocyanuric acid or trichloroisocyanuric acid ("TCCA").

When the halogenating agent is a N-halosuccinimide, the halogenating agent may be selected from N-chlorosuccinimide or N-bromosuccinimide.

When the halogenating agent is a hypochlorite, the halogenating agent may be selected from sodium hypochlorite or calcium hypochlorite.

When the halogenating agent is a N-halo-p-toluenesulfonamide salt, the halogenating agent may be a N-chloro-p-toluenesulfonamide sodium salt.

The halogenating agent should be used in step (c) in an amount of about 0.5 equivalent to less than about 1 equivalent, based on 1 equivalent of the beta-ester of aspartic acid.

The conditions for step (c) should be basic through the introduction of alkali, room temperature up to about 40° C. for about 1 hour to about 24 hours, desirably about 2 hours to about 16 hours, such as about 4 to about 6 hours.

The yield of the cyanoacetate should be greater than about 30%, such as greater than about 40%, desirably above about 85%.

For the optional steps of (b) and (d) appropriate isolation and/or separation techniques may be used to isolate the intermediate beta-ester of aspartic acid from step (b) or the cyanoacetate from step (d).

Together with the aspartic acid as an initial reactant in the inventive process is an alcohol, as noted above. The alcohol should be used in an amount of about 12 to about 17 equivalents.

The alcohol and the aspartic acid should be used in a molar ratio of about 0.5 to about 2 equivalents, such as about 0.8 equivalents.

While the time of reaction is generally given above, the time may be monitored by reference to the formation of the desired product using NMR spectrometry, as noted in the Examples. The time of reaction may be adjusted depending on the identity of the specific reactants, the scale of the reaction and whether heat is added to the reaction conditions.

The following examples are intended to illustrate but in no way limit the present invention.

EXAMPLES

Example 1

We used reaction conditions reported in K. Sato et al., *Chem. Commun.*, 51, 9946-48 (2015) to selectively esterify aspartic acid at the beta carboxylic acid, along the synthetic scheme set forth below:

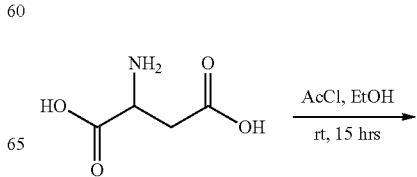

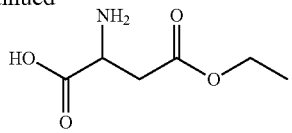

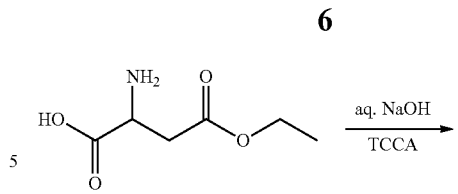

Applying the synthesis conditions of Sato et al. the beta-ethyl ester of aspartic acid was obtained in 54.6% yield, as shown below in Table (Entry 1). The remaining entries vary amounts of acetyl chloride and/or ethanol, and in some instances a reduced reaction time. Table 1 below shows each of the seventeen entries, all having 1 equivalent of aspartic acid (25 grams) and conducted at room temperature.

TABLE 1

| Entry | AcCl (eq) | EtOH (eq) | Time (hrs) | Yield (%) |
|---|---|---|---|---|
| 1 | 4.0 | 34 | 15 | 54.6 |
| 2 | 2.0 | 34 | 15 | 61.5 |
| 3 | 4.0 | 17 | 15 | 78.5 |
| 4 | 2.0 | 17 | 15 | 86.5 |
| 5 | 2.0 | 17 | 15 | 96.8 |
| 6 | 2.0 | 17 | 15 | 89.4 |
| 7 | 3.0 | 17 | 15 | 89.4 |
| 8 | 3.0 | 17 | 15 | 77.5 |
| 9 | 2.0 | 10 | 15 | 54.9 |
| 10 | 2.0 | 8 | 15 | 68.3 |
| 11 | 2.0 | 10 | 15 | 72.3 |
| 12 | 2.0 | 12 | 15 | 85.3 |
| 13 | 2.0 | 14 | 15 | 84.4 |
| 14 | 2.0 | 17 | 8 | 28.9 |
| 15 | 2.0 | 17 | 12 | 75.7 |
| 16 | 2.0 | 14 | 8 | 64.3 |
| 17 | 2.0 | 14 | 12 | 97.1 |

Table 2 shows each of the 8 entries, all having 1 equivalent of aspartic acid (2.66 grams), 17 equivalents of ethanol and conducted at room temperature. The lower reaction times (e.g., 2-4 hours) (Entries 1-6) show the formation on the beta-ethyl ester did not occur, therefore reaction times in excess of 15 hours are desirable to enable greater beta-ethyl ester formation.

TABLE 2

| Entry | AcCl | Time (hr) | Yield (%) |
|---|---|---|---|
| 1 | 2.0 eq | 4 | — |
| 2 | 1.5 eq | 4 | — |
| 3 | 1.2 eq | 4 | — |
| 4 | 1.5 eq | 4 | — |
| 5 | 1.2 eq | 4 | — |
| 6 | 1.2 eq | 2 | — |
| 7 | 1.2 eq | 15 | 41.0 |
| 8 | 1.5 eq | 15 | 51.8 |

Confirmation of formation of the ethyl ester of aspartic acid at only the beta carboxylic acid was obtained by NMR spectral analyses: $^1$H NMR (301 MHz, $D_2O$) δ 4.39-4.31 (m, 2H), 4.19 (qd, J=7.2, 1.7 Hz, 5H), 3.09 (dd, J=5.3, 3.9 Hz, 4H), 1.22 (t, J=7.1 Hz, 8H) and $^{13}$C NMR (76 MHz, $D_2O$) δ 171.36, 170.86, 62.63, 49.24, 34.09, 13.09.

Example 2

G. Hiegel et al., *Synth. Commun.*, 34, 3449-53 (2004) report the use of trichloroisocyanuric acid ("TCCA") to facilitate the oxidative decarboxylation of amino acids to nitriles according to the synthetic scheme set forth below.

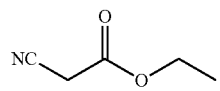

Applying the synthesis conditions of Hiegel et al., we applied 0.66 equivalents of TCCA to 1 equivalent of the beta-ethyl ester of aspartic acid under the reaction conditions listed in Table 3 below. Changing the time, base concentration, temperature and TCCA concentration did not improve the results recorded in Table 3, Entry 1, which was a yield of 85%.

TABLE 3

| Entry | NaOH (mL) | Time (h) | Temp. (° C.) | Yield (%) |
|---|---|---|---|---|
| 1 | 2N aq. (5 mL) | 6 | rt | 85 |
| 2 | 2N aq. (5 mL) | 2 | rt | 30 |
| 3 | 2N aq. (5 mL) | 4 | rt | 36 |
| 4 | 2N aq. (5 mL) | 16 | rt | 24 |
| 5 | 2N aq. (5 mL) | 6 | rt | 37 |
| 6 | 2N aq. (10 mL) | 6 | rt | trace |
| 7 | 2N aq. (5 mL) | 6 | rt | 15 |
| 8 | 2N aq. (5 mL) | 6 | 40 | 44 |
| 9 | 4N aq. (5 mL) | 2 | rt | trace |
| 10 | 4N aq. (5 mL) | 4 | rt | trace |

For Entry 7, though the details of the reaction are the same, the TCCA was added at 0° C. rather than at room temperature as in Entry 1, and the yield decreased to 15%.

Example 3

In a one-pot continuous reaction, aspartic acid was converted directly to ethyl cyanoacetate without isolating or separating the beta-ethyl ester of aspartic acid that formed as an intermediate. More specifically, 1 equivalent of aspartic acid was mixed in ethanol (17 equivalents for Entry 1 and 14 equivalents for Entry 2) in the presence of 2 equivalents of acetyl chloride at room temperature for a period of time of about 12 to about 15 hours. TCCA (0.66 equivalents) in 15 mls of 2N NaOH and 5 mls of acetonitrile were then introduced to the reaction, and stirring was allowed to continue for a period of time of about 21 hours.

The one-pot continuous synthesis obtained an overall yield of 39% for Entry 1 and 49% for Entry 2. $^1$H NMR confirmed the presence of the ethyl cyanoacetate; GC-FID showed the product had a purity of 92% from an organic extraction of the reaction mixture without distillation.

What is claimed is:

1. A process for the preparation of a cyanoacetate, steps of which comprise:
   (a) contacting aspartic acid with an alcohol, in the presence of an acetyl halide, under appropriate conditions and for a time sufficient to yield a beta-ester of the aspartic acid;
   (b) optionally, separating therefrom the so formed beta-ester of the aspartic acid;
   (c) contacting the beta-ester of the aspartic acid with a halogenating agent under appropriate conditions and for a time sufficient to yield a cyanoacetate; and (d) optionally, separating therefrom the so formed cyanoacetate.

2. The process of claim 1, wherein the cyanoacetate is a $C_{1-20}$ alkyl cyanoacetate, a $C_{6-20}$ aryl cyanoacetate, a $C_{7-20}$ alkaryl cyanoacetate or a $C_{7-20}$ aralkyl cyanoacetate, any of which may be substituted by one or more hydroxyl groups or $C_{1-20}$ alkyl ether groups.

3. The process of claim 1, wherein the cyanoacetate is a $C_{1-20}$ alkyl cyanoacetate, wherein the $C_{1-20}$ alkyl may contain one or more points of unsaturation and may be substituted and/or interrupted by one or more heteroatoms or heteroatom-containing groups, or substituted by halogens or substituted or interrupted by halogen-containing groups.

4. The process of claim 1, wherein the cyanoacetate is a $C_{1-20}$ alkyl cyanoacetate selected from methyl cyanoacetate, ethyl cyanoacetate, propyl cyanoacetates, butyl cyanoacetates, pentyl cyanoacetates, octyl cyanoacetates, alkoxy ether alkyl cyanoacetates, allyl cyanoacetates, and combinations thereof.

5. The process of claim 1, wherein the cyanoacetate is a $C_{6-20}$ aryl cyanoacetate selected from phenyl cyanoacetate.

6. The process of claim 1, wherein the cyanoacetate is a $C_{7-20}$ aralkyl cyanoacetate selected from phenethyl cyanoacetate, benzyl cyanoacetate, or toluyl cyanoacetate.

7. The process of claim 1, wherein the alcohol is an alkyl alcohol, an aryl alcohol, an alkaryl alcohol or an aralkyl alcohol.

8. The process of claim 1, wherein the alcohol is selected from methanol, ethanol, propanols, proparganols, butanols, pentanols, hexanols, octanols, nonanols, oxononanols, decanols, dodecanols, allanol, cyclohexanol, tetrahydrofurfurol, chloroethanol, 2,2,2-trifluoroethanol, hexafluoroisopropanol, alkoxy ether alkanols, dialkyl siloxanols, or trialkylsilylalkanols.

9. The process of claim 1, wherein the alcohol is an aromatic alcohol.

10. The process of claim 1, wherein the alcohol is selected from phenol, benzyl alcohol or derivatives thereof.

11. The process of claim 1, wherein the acetyl halide is selected from acetyl bromide or acetyl chloride.

12. The process of claim 1, wherein the beta-ester of the aspartic acid is a beta-alkyl ester.

13. The process of claim 1, wherein the beta-ester of the aspartic acid is selected from beta-methyl ester of aspartic acid, beta-ethyl ester of aspartic acid, a beta-propyl ester of aspartic acid, a beta-butyl ester of aspartic acid, a beta-pentyl ester of aspartic acid, a beta-octyl ester of aspartic acid, a beta-alkoxy ether ester of aspartic acid, a beta-allyl ester of aspartic acid, a beta-phenyl ester of aspartic acid or a beta-phenethyl ester of aspartic acid.

14. The process of claim 1, wherein the halogenating agent is selected from trihaloisocyanuric acid, N-halosuccinimide, hypochlorites and N-halo-p-toluenesulfonamide salts.

15. The process of claim 1, wherein the halogenating agent is selected from tribromoisocyanuric acid or trichloroisocyanuric acid.

16. The process of claim 1, wherein the halogenating agent is selected from N-chlorosuccinimide or N-bromosuccinimide.

17. The process of claim 1, wherein the halogenating agent is selected from sodium hypochlorite or calcium hypochlorite.

18. The process of claim 1, wherein the halogenating agent is selected from N-chloro-p-toluenesulfonamide sodium salt.

19. The process of claim 1, wherein the beta-ester of the aspartic acid is formed preferentially to an alpha-ester of the aspartic acid.

20. The process of claim 1, wherein the beta-ester of the aspartic acid is formed in an amount of greater than about 80%.

21. The process of claim 1, wherein the beta-ester of the aspartic acid is formed in an amount of greater than about 90%.

22. The process of claim 1, wherein for each equivalent of the beta-ester of the aspartic acid between about 2 to about 3 equivalents of acetyl halide and between about 12 and about 17 equivalents of alcohol are used in step (a).

23. The process of claim 1, wherein step (b) is substantially free from the aspartic acid and/or the acetyl halide, and/or halogenating agent, and by-products.

24. The process of claim 1, wherein step (d) is substantially free from the aspartic acid, the acetyl halide, and/or halogenating agent, and by-products.

* * * * *